(12) United States Patent
Krulevitch et al.

(10) Patent No.: US 6,991,963 B2
(45) Date of Patent: *Jan. 31, 2006

(54) ELECTRONIC UNIT INTEGRATED INTO A FLEXIBLE POLYMER BODY

(75) Inventors: Peter A. Krulevitch, Pleasanton, CA (US); Mariam N. Maghribi, Livermore, CA (US); William J. Benett, Livermore, CA (US); Julie K. Hamilton, Tracy, CA (US); Klint A. Rose, Mt. View, CA (US); James Courtney Davidson, Livermore, CA (US); Mark S. Strauch, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/835,226

(22) Filed: Apr. 28, 2004

(65) Prior Publication Data

US 2004/0209396 A1    Oct. 21, 2004

Related U.S. Application Data

(63) Continuation of application No. 10/323,219, filed on Dec. 18, 2002, now Pat. No. 6,878,643.

(51) Int. Cl.
H01L 21/44 (2006.01)

(52) U.S. Cl. .......................... 438/106; 438/55
(58) Field of Classification Search .................. 438/55, 438/53, 6, 7, 25, 106, 780
See application file for complete search history.

(56) References Cited

U.S. PATENT DOCUMENTS

| | | | | |
|---|---|---|---|---|
| 5,051,275 | A | * | 9/1991 | Wong .......................... 427/58 |
| 5,215,801 | A | * | 6/1993 | Wong .......................... 428/76 |
| 5,346,850 | A | | 9/1994 | Kaschmitter et al. |
| 5,395,481 | A | | 3/1995 | McCarthy |
| 5,399,231 | A | | 3/1995 | McCarthy |
| 5,505,321 | A | | 4/1996 | Caron et al. |
| 5,591,519 | A | | 1/1997 | Caron et al. |
| 5,644,207 | A | | 7/1997 | Lew et al. |
| 5,674,758 | A | | 10/1997 | McCarthy |
| 5,817,550 | A | | 10/1998 | Carey et al. |
| 6,201,980 | B1 | | 3/2001 | Darrow et al. |
| 6,596,569 | B1 | * | 7/2003 | Bao et al. ................... 438/151 |
| 2001/0045362 | A1 | | 11/2001 | Deng et al. |
| 2002/0045030 | A1 | | 4/2002 | Ozin et al. |
| 2002/0050220 | A1 | | 5/2002 | Schueller et al. |
| 2002/0064841 | A1 | | 5/2002 | Klemic et al. |
| 2002/0064909 | A1 | | 5/2002 | Graclas et al. |

FOREIGN PATENT DOCUMENTS

WO    WO 01/70389 A2    9/2001

* cited by examiner

Primary Examiner—David Nelms
Assistant Examiner—Quoc Hoang
(74) Attorney, Agent, or Firm—Eddie E. Scott; Alan H. Thompson

(57) ABSTRACT

A peel and stick electronic system comprises a silicone body, and at least one electronic unit operatively connected to the silicone body. The electronic system is produce by providing a silicone layer on a substrate, providing a metal layer on the silicone layer, and providing at least one electronic unit connected to the metal layer.

4 Claims, 7 Drawing Sheets

ELECTRONIC UNIT INTEGRATED INTO A FLEXIBLE POLYMER BODY

CROSS-REFERENCE TO RELATED APPLICATIONS

This application is a continuation of U.S. patent application Ser. No. 10,323,219 filed Dec. 18, 2002, titled, "Electronic Unit Integrated into a Flexible Polymer Body." now U.S. Pat. No. 6,878,643. The related applications are both commonly assigned to The Regents of the University of California.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to electronic systems and more particularly to a system that comprises an electronic unit integrated into a flexible polymer body.

2. State of Technology

Low cost components, sensors, and electronic systems are desirable for numerous defense, consumer, and other applications. This includes electronic components, sensors, electronic systems, disposable electronic devices and methods of manufacturing them. The overall price of a component, sensor, electronic system is determined primarily by integration and packaging costs, not the cost of individual elements. The packaging performs two functions: it provides a means for interconnecting various components together, and it protects delicate components from the environment.

U.S. Pat. No. 5,817,550 for a method for formation of thin film transistors on plastic substrates to Paul G. Carey, Patrick M. Smith, Thomas W. Sigmon, and Randy C. Aceves issued Oct. 6, 1998 and assigned to Regents of the University of California provides the following background information, "Recently a process was developed for crystallizing and doping amorphous silicon on a low cost, so-called low-temperature plastic substrate using a short pulsed high energy source in a selected environment, without heat propagation and build-up in the substrate so as to enable use of plastic substrates incapable of withstanding sustained processing temperatures higher than about 180 degree C."

SUMMARY

Features and advantages of the present invention will become apparent from the following description. The invention provides an electronic apparatus comprising a flexible polymer body and an electronic unit integrated into the flexible polymer body. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention comprises an electronic apparatus and a method of processing and producing an electronic apparatus. The electronic apparatus comprises a flexible polymer body and an electronic unit operatively connected to the flexible polymer body. The method of processing and producing an electronic apparatus comprises implementing initial processing steps on a flexible polymer body and providing electronic components connected to the flexible polymer body.

The drawings and written description illustrate a number of specific embodiments of the invention. These embodiments and other embodiments give a broad illustration of the invention. Various changes and modifications within the spirit and scope of the invention will become apparent to those skilled in the art. One embodiment comprises a silicone body and an electronic unit integrated into said silicone body. The electronic unit comprises various systems including, but not limited to, a sensor, a MEMS sensor, a radio, a recorder, a recorder and player, a camera, a video camera, a video player, a video recorder, a video recorder and player, a cell phone, a computer, a calculator, a phone tap, a device that detects phone taps, an audio surveillance device, a medical device, a biosensor, and a radiation monitor. The electronic unit also comprises various components including, but not limited to, a power source, a battery, a solar cell, wireless electronics for communication, a capacitor, a resistor, an inductor, a transformer, an integrated circuit, a microprocessor, a digital to analog converter, a display, and other components. Another embodiment comprises a method of fabricating an electronic apparatus comprising a silicone layer on a substrate, providing a patterned metal layer on said silicone layer, providing a second layer of silicone on the flexible polymer layer, and operatively connecting at least one electronic unit to the patterned metal layer and the second silicone layer.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
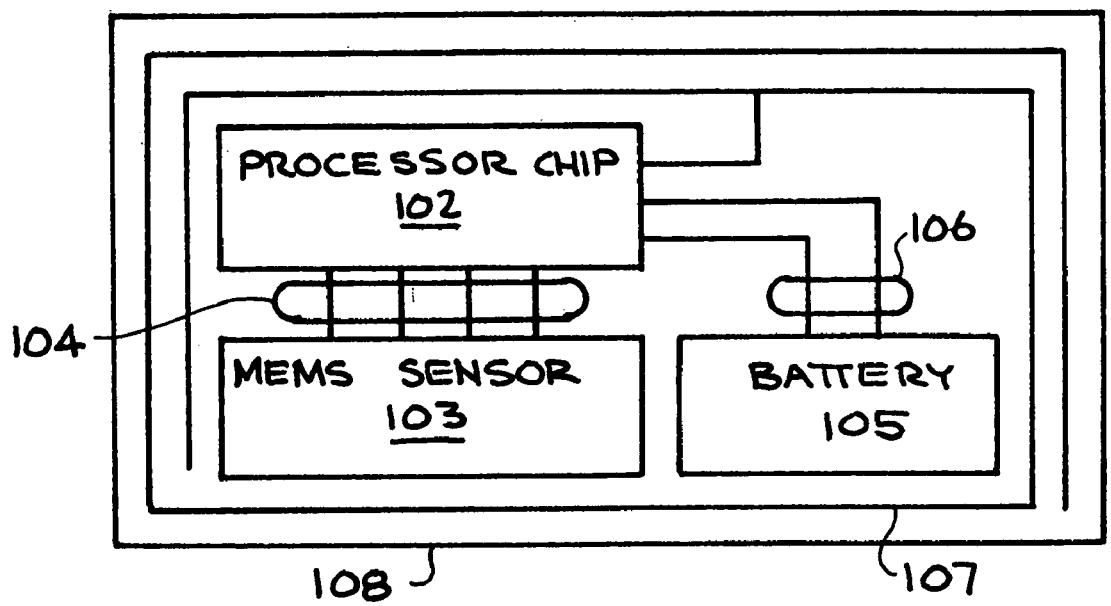
FIG. 1 illustrates an embodiment of a system incorporating the present invention.

Referring now to the drawings, to the following detailed information, and to incorporated materials; a detailed description of the invention, including specific embodiments, is presented. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention comprises an electronic apparatus and a method of processing and producing an electronic apparatus. The electronic apparatus comprises a flexible polymer body and an electronic unit operatively connected to the flexible polymer body. The method of processing and producing an electronic apparatus comprises implementing initial processing steps on a flexible polymer body and providing electronic components operatively connected to the flexible polymer body.

The drawings and written description illustrate a number of specific embodiments of the invention. These embodiments and other embodiments give a broad illustration of the invention. Various changes and modifications within the spirit and scope of the invention will become apparent to those skilled in the art. One embodiment comprises a flexible polymer body and an electronic unit integrated into said flexible polymer body. The invention is incorporated in various systems including, but not limited to, a sensor, a MEMS sensor, a radio, a recorder, a recorder and player, a camera, a video camera, a video player, a video recorder, a video recorder and player, a cell phone, a computer, a calculator, a phone tap, a device that detects phone taps, an audio surveillance device, a medical device, a biosensor, and a radiation monitor. The invention is also incorporated into various components including, but not limited to, a power source, a battery, a solar cell, wireless electronics for communication, a capacitor, a resistor, an inductor, a transformer, an integrated circuit, a microprocessor, a digital to analog converter, a display, and other components.

Referring now to in FIG. 1, one embodiment of a system constructed in accordance with the present invention is illustrated. The system is generally designated by the reference numeral 100. The system 100 comprises a flexible polymer body 101, a first unit 102 operatively connected to the flexible polymer body, an additional unit 103 operatively connected to the flexible polymer body, and a circuit 104 integrated into the flexible polymer body connecting the first unit 102 and the additional unit 103.

The system 100 provides an integrated electronic system that can be described as a "peel and stick" sensor system. The system 100 can be visualized as a thin, clear, and flexible unit similar to the clear "peel and stick" tags garages place on an automobile's windshield after the car has been serviced to remind the owner of the automobile when the next servicing is due. The thin, clear, and flexible "peel and stick" electronic apparatus 100 can be very small and inconspicuous. The electronic apparatus 100 can be removed easily without leaving any residue behind.

The system 100 comprises a flexible polymer body 101. The flexible polymer body can be a number of polymers whose properties are determined by the organic groups forming the polymer and that have characteristics that include one or more of being fluid, resinous, rubbery, stable in high temperatures, and hydrophobic. The flexible polymer body 101 shown in FIG. 1 is a silicone body. The flexible polymer body 101 is made of poly(dimethylsiloxane) known as PDMS. A MEMS sensor 103 is integrated into the flexible polymer body 101. MEMS or MicroElectroMechanical Systems are known as systems that contain extremely small mechanical elements, often integrated together with electronic processing circuitry. MEMS have feature sizes that are typically measured in micrometers (microns), that is, millionths of a meter. As a reference, the diameter of human hair is about 100 microns. MEMS sensors have a wide variety of applications. For example uses of MEMS sensors include detecting movement, detecting sound, gyroscopes, accelerometers, micro-optical systems, fiber-optic communications, super-fast electrophoresis systems for DNA separation, video projection chips, magnetometers, micro-robots, micro-tweezers, neural probes, and many other uses. MEMS sensors are used to detect automobile collisions and deploy airbags, and magnetometers that can detect the presence of military equipment such as tanks, trucks or even a soldier. The table below illustrates some of the uses of MEMS sensors.

TABLE I

| Type | Examples |
| --- | --- |
| Acceleration and Vibration Sensing | Instruments, sensors and equipment for producing, controlling or measuring vibratory or oscillatory motion |
| Acoustic Sensing | Sensors and instruments for measuring and transmitting sound levels and frequency |
| Analytical Sensors | Sensors that are used to analyze material samples, or their components, and record data specific to the application |
| Density and Specific Gravity Sensing | For determining density and specific gravity including hydrometers, digital instruments, pycnometers, etc. |
| Displacement Sensing | Detect (optical, Hall effect, inductive, etc.) or measure changes in displacement |
| Electrical and Electromagnetic Sensing | Devices used to detect and measure electrical and electromagnetic signals |
| Encoders and Resolvers | Motion feedback devices providing position and velocity information to closed-loop control systems |

TABLE I-continued

| Type | Examples |
|---|---|
| Environmental Sensors | Sensors designed to measure and test for changes in environmental conditions, including radiation (both wavelength and as a hazardous emission), temperature, moisture and dew point, smoke, dust and opacity, light, weather, and water quality |
| Flow Sensing | Electronic devices designed to monitor the physical flow of liquids, gases or solids; and to convert this data into electronic signals |
| Force Sensing | Instruments, sensors and equipment for measuring static or dynamic force or torque |
| Gas Sensing | Measuring the amount of a specific gas or gases in a given environment |
| Humidity and Moisture Sensing | Instruments, sensors, indicators or controllers for measuring humidity, moisture content and weather conditions |
| Level Sensing | Devices used to detect or measure level of liquids, gases or solids, within pipes or tanks, or to detect the interfaces between different materials |
| Linear Position Sensing | Devices used to measure the linear displacement of an object |
| Orientation Position Sensing | Sensors and instruments used to detect rotary position, angular position, tilt, or inclination relative to the horizon or a linear position |
| Pressure Sensing | Instruments and sensors for measuring or controlling the pressure applied to a surface from a liquid, bulk material or discrete component |
| Proximity or Presence Sensing | Sensors and Instruments for proximity sensing, including capacitive, photoelectric, inductive, Hall effect, ultrasonic, and other technologies |
| Rotary Position Sensing | Devices and instruments for sensing and measurement of angular motion, speed, and position; includes encoders, resolvers, synchros and similar devices |
| Temperature Sensing | Devices that are designed to detect or measure changes in temperature such as temperature probes, sensors, etc. |
| Tension Sensing | Instruments and controllers that measure, monitor or adjust tension in cable, fiber, belts, sheets and other webs |
| Tilt Sensing | Sensors or instruments that detect inclination relative to the horizon, rotary position, angular rates or linear acceleration |
| Torque Sensing | Instruments and controllers that measure, monitor or adjust torque in shafts, cables, fibers, rods and other components |
| Velocity Sensing | Instruments and controllers that measure, monitor or adjust velocity or speed in shafts, moving webs and other components |
| Vibration and Acceleration Sensing | Instruments, sensors and equipment for producing, controlling or measuring oscillatory or vibratory motion |
| Viscosity Sensing | Instruments and sensors for measuring the viscosity or viscoelastic properties of liquid or molten glass and plastic |
| Vision Sensing | CCD, CMOS or other image capturing sensors that form the heart of a digital camera or imaging system |
| Weather Sensing | Instruments or sensors designed to measure one or multiple components of weather; including wind speed and direction, rain/snow fall, solar radiation, temperature, pressure and humidity |

Examples of some of the electronic systems that are utilized in different embodiments of the invention include the following: implantable medical device, radio, recorder, recorder and player, video camera, video player, video recorder, video recorder and player, cell phone, computer, calculator, phone tap, device that detects phone taps, audio surveillance device, medical device, biosensor, radiation monitor, which include components such as a power source, battery, solar cell, wireless electronics for communication, capacitor, resistor, inductor, transformer, integrated circuit, microprocessor, digital to analog converter, display, camera, cell phone, and other electronic devices. Discrete components such as batteries, solar cells, displays and microprocessors can be integrated together to form electronic systems.

Referring again to FIG. 1, the flexible polymer body comprises a poly(dimethylsiloxane) (PDMS) body 101 that serves as a polymer-based platform for integrating and packaging individual components. A MEMS sensor 103 is integrated into the flexible polymer body 101. A processor chip 102 is operatively connected and integrated into the flexible polymer body 101. A battery 105 provides power to the processor chip 102 and the MEMS sensor 103. The processor chip 102 and MEMS sensor 103 are connected by the metalization system 104. The battery 105 that provides power to the processor chip 102 and the MEMS sensor 103 is connected to the processor chip 102 and MEMS sensor 103 by metalization system 106. An antenna 107 allows information that has been obtained by the MEMS sensor 103 to be transmitted to a remote receiver. The antenna 107 is connected to the processor chip 102. The underside 109 of the substrate or body 101 is a peel and stick surface that can easily be affixed to other surfaces. In manufacturing, after curing the PDMS body surface 109 is tacky and will stick to any clean, smooth surface such as windows, eyeglasses, monitors, cars, and a wide variety of other surfaces. The electronic apparatus 100 can be removed easily without leaving any residue behind. An adhesive may be included on the underside surface 109 or the underside surface 109 may be attached to other surfaces by other means. The small, thin, clear, flexible, peel and stick, electronic apparatus 100 is very inconspicuous and durable. The flexible polymer body 101 protects delicate components from the environment. Specifically, devices that are bonded to the polymer body are sealed and protected from moisture, splashes, and water immersion. The processor chip 102 and the other components are irreversibly bonded to the PDMS substrate 101 to make electrical contact to the metal traces 104 and 106 and seal the device 100, protecting active elements from the environment.

Figure 2:
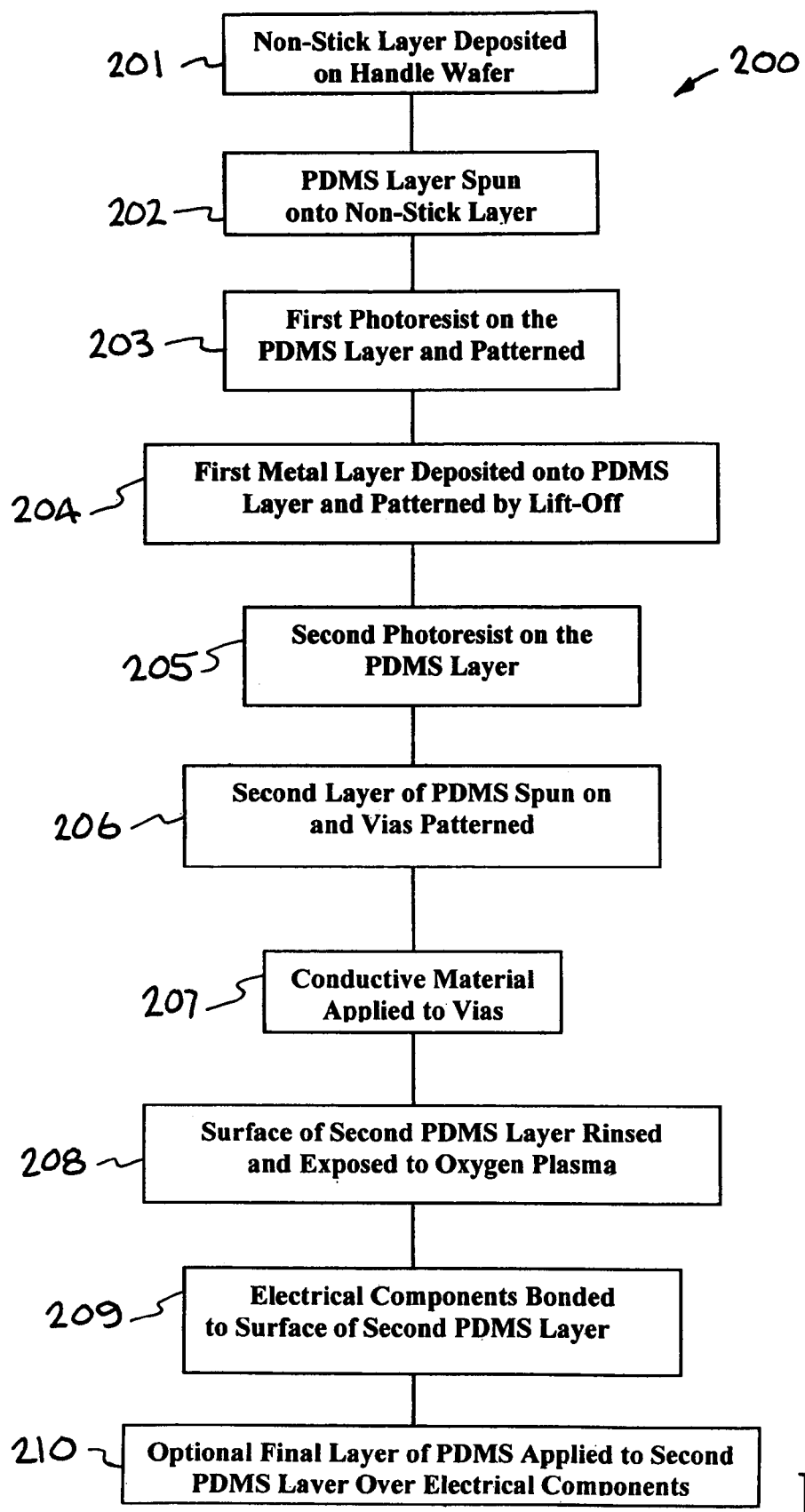
FIG. 2 illustrates an embodiment of a method of producing a system of the present invention.

Referring now to FIG. 2, an embodiment of a method of the present invention is illustrated. The embodiment is designated generally by the reference numeral 200. The embodiment 200 comprises a method of producing the electronic system 100 shown in FIG. 1. The method 200 and the electronic system 100 produced by the method are inexpensive. The method 200 provides rapid turn-around and is amenable to batch processing.

Low cost electronic systems and methods of producing electronic systems are desirable for numerous defense, consumer, and other applications. This includes electronic components, sensors, and electronic systems. The overall price of an electronic component, sensor, or electronic system is determined primarily by integration and packaging costs, not the cost of individual elements. The packaging performs two functions: it provides a means for interconnecting various components together, and it protects delicate components from the environment.

In step 202, a liquid pre-polymer layer is spun onto a silicon handle wafer and cured to form a flexible polymer. A polymer is a chemical compound with high molecular weight consisting of a number of structural units linked together by covalent bonds. The polymer used for the flexible polymer body has characteristics that include at least one of being fluid, resinous, rubbery, stable in high temperatures, and hydrophobic. The flexible polymer is a silicone. The silicone is poly(dimethylsiloxane) known as PDMS. PDMS has very low water permeability and protects the electronic components from the environment. PDMS is flexible and will conform to curved surfaces. It is transparent, stretchable, resinous, rubbery, stable in high temperatures and provides numerous applications for the electronic system 100 produced by the method 200.

The silicon handle wafer provides a temporary base for production of the electronic system 100. Silicon wafers are convenient for the handle material because they are flat, stable, routinely used in microfabrication applications, and they are readily available. However, other materials such as glass, plastic, or ceramic could be used as well. The electronic system 100 will eventually need to be removed from the handle wafer. Since the flexible polymer layer could adhere to the surface of the silicon handle wafer, a non-stick layer is first provided on the silicon handle wafer.

Step 201 comprises the deposition of gold (or platinum) onto the handle wafer. The gold film facilitates removal of the polymer membrane from the wafer after completion of the fabrication process. A 2 mm wide ring at the edge of the silicon wafer is left without the gold coating to prevent the PDMS membrane from lifting off during processing. PDMS is then spun onto the wafer at a desired thickness and cured. For example the PDMS may be cured at 66° C. for 24–48 hours. It is to be understood that the step 201 could be omitted if the surface on which the PDMS layer is deposited is such that the PDMS will not become bonded.

In step 203 the process of forming the electrical circuit lines and the antenna of the electronic system 100 is initiated. A photoresist (AZ®1518, Clariant) is spun onto the PDMS membrane surface at 1000 rpm for 20 seconds and baked at 60° C. for 20 minutes. The temperature is brought down slowly (30 min to ramp temperature down) to room temperature to avoid cracking in the photoresist. Prior to photoresist application, the wafer is placed in an oxygen plasma to activate the surface. This allows the resist to wet the PDMS surface preventing beading and ensuring the formation of a smooth and uniform coat of photoresist on the polymer surface. The substrate is placed in the oxygen plasma for 1 minute at an RF power of 100 Watts with oxygen flowing at 300 sccm. The photoresist features are then UV exposed at 279 mJ and developed in AZ developer mixed 1:1 with water for 70 sec. Then the wafer is rinsed under a gentle stream of water and dried using N2. The wafer is placed for a second time in the oxygen plasma to activate the newly exposed PDMS surface, and promote adhesion of the metal, which is deposited in the next step.

In step 204 a 150 nm gold film is e-beam evaporated onto the wafer using 20 nm of titanium as the adhesion layer. Both titanium and gold are deposited at 0.2 nm per second. The e-beam needs to be sufficiently cooled down before removing the parts. Cool down is conducted for 10 min. under vacuum and for 20 min. with the system vented, but not open. The metal adheres to the PDMS surface in regions where the photoresist was removed, and the excess metal is removed through a lift-off process by placing the wafer in acetone. The wafer is then prepared for the next step by rinsing with ethanol and drying gently. If the PDMS surface is contaminated or aged, it can be refreshed by soaking in a 20% solution of HCl for 8 min.

In steps 205 and 206 the process of forming the vias through a passivating layer of PDMS to connect the electrical circuit lines to the electronic components of the electronic system 100 is initiated. A photoresist (AZ®1518, Clariant) is spun onto the PDMS membrane surface. The photoresist via features are then patterned by exposing the resist to UV (279 mJ) through a photomask and developing in AZ developer mixed 1:1 with water for 70 sec. The passivating layer of silicone is spun onto the wafer, over the patterned photoresist, then cured for twenty four hours at 66 C. The surface is gently swabbed to remove excess PDMS from the top of the photoresist features before stripping the resist. This ensures the removal of the photoresist and the complete clearance of the vias. To strip the resist the wafer is soaked in acetone for 15 min., soaked in isoproponol for 5 min., and then rinsed with isoproponol and dried.

In step 207 conductive material is applied to the vias. The vias can be filled with conductive silicone adhesive, conductive ink or solder paste. An automated dispenser or applicator machine is used to deposit precise amounts of material in the vias locations. Alternatively, the conductive material can be screen-printed using conductive inks, or liquid ink can be injected into channels formed in the first PDMS layer. As another option, metal can be electroplated in the PDMS vias to form an array of electrical contacts.

In step 208, the surface of the second PDMS layer is rinsed with ethanol and exposed to an oxygen plasma. This activates the surface in preparation for bonding the electronic components to the PDMS. The following step is performed in a nitrogen environment in order to extend the lifetime of the activated surface.

In step 209, one or more components are bonded to the PDMS surface in order to make electrical contact and to seal and protect the underlying surface of the devices from the environment.

In step 210 the final layer of PDMS is applied to the second PDMS layer over the electrical components. This step is not required in all applications. This protects delicate components from the environment. The electronic system 100 is then removed from the handle wafer. The bottom surface of the electronic system 100 where it is removed from the handle wafer is tacky and will stick to any clean, smooth surface such as windows, eyeglasses, monitors, cars, and a wide variety of other surfaces without leaving a residue. An adhesive may be included on the body surface or the body surface may be attached to other surfaces by other means. The small, thin, clear, flexible, peel and stick, electronic apparatus 100 is very inconspicuous and durable. The PDMS body protects delicate components from the environment without the need for additional packaging.

Figure 3:
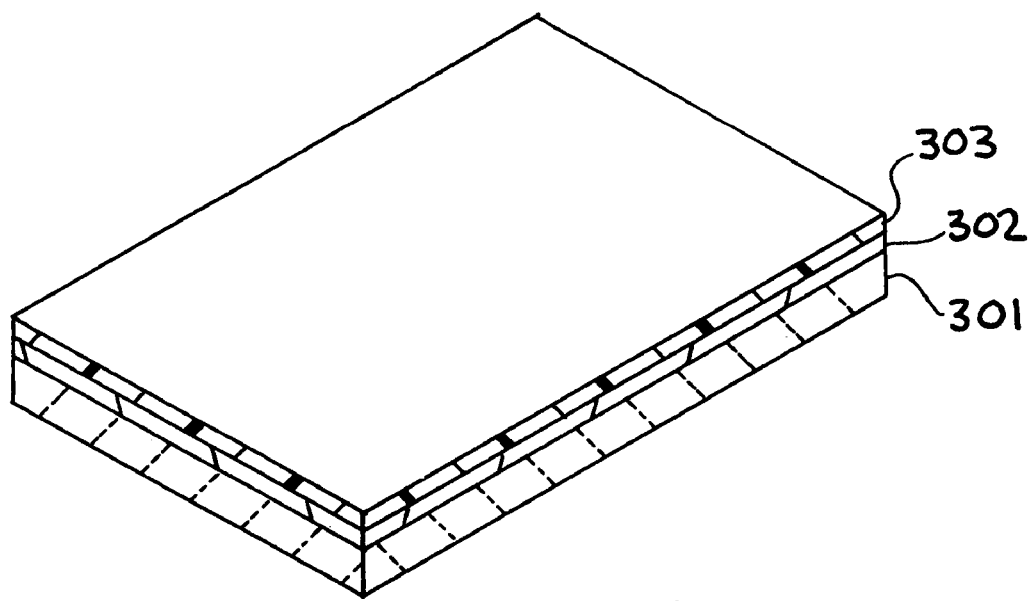
FIG. 3 is an illustration showing how a non-stick layer is applied to a silicon handle wafer 301 and a flexible polymer layer is applied to the non-stick layer.

Referring now to FIG. 3, an illustration is provided showing how a non-stick layer 302 is applied to a silicon handle wafer 301 and a flexible polymer layer 303 is applied to the non-stick layer. A silicon handle wafer 301 provides a temporary base for production of the electronic system. A non-stick layer in the form of gold or platinum is deposited onto the handle wafer 301. This allows for removal of the flexible polymer body from the handle wafer after processing. A 2 mm wide ring at the edge of the silicon wafer is left without the gold coating to prevent the flexible polymer membrane from lifting off the substrate during processing. The first flexible polymer layer 303 is spun onto the non-stick layer 302 at a desired thickness and cured. For example the flexible polymer may be cured at 66° C. for 24–48 hours.

Figure 4:
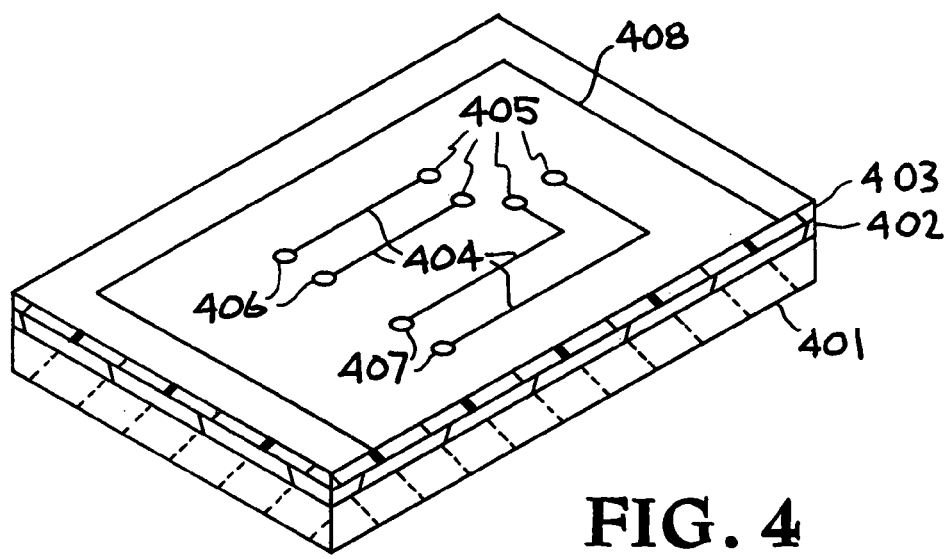
FIG. 4 is an illustration showing vias that are used to produce connections to electrical circuit lines to electronic components.

Referring now to FIG. 4, an illustration is provided showing the vias that are used to form connectors for connecting the electrical circuit lines to each other and to the electronic components of the electronic system. A silicon handle wafer 401 is coated with a non-stick layer 402 and a flexible polymer layer 403 is deposited on top of the non-stick layer 402. Conductive lines 404 provide the circuits for connecting the electrical components and the antenna 408. Vias are formed using the photoresist during manufacture to provide connectors 405, 406, and 407 that are connected to the conductive lines 404. The connectors 405, 406, and 407 are used to provide electrical connection to the three electrical components. The connectors 405 connect the processor chip. The connectors 406 connect the MEMS sensor. The connectors 407 connect the battery.

Figure 5:
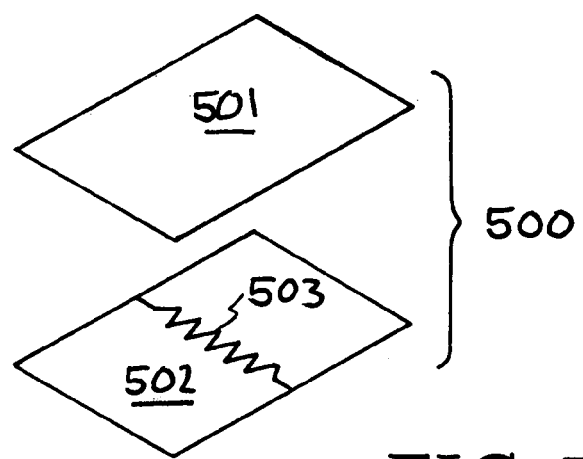
FIG. 5 illustrates another embodiment of a system constructed in accordance with the present invention.

Referring now to in FIG. 5, another embodiment of a system constructed in accordance with the present invention is illustrated. The system is generally designated by the reference numeral 500. The system 500 comprises a flexible polymer body 501 & 502 and a resistor 503 operatively connected to the flexible polymer body.

The system 500 comprises a flexible polymer body 501 & 502. The flexible polymer body can be a number of polymers whose properties are determined by the organic groups and that have characteristics that include one or more of being fluid, resinous, rubbery, stable in high temperatures, and hydrophobic. The flexible polymer body unit 501 comprises a polymer substrate that serves as a polymer-based platform for integrating and packaging the resistor 503. The resistor 503 is integrated into the flexible polymer body 501 & 502. The system 500 can provide a wide variety of other electronic components instead of the resistor 503. For example, electronic components that can be used in place of resistor 503 include capacitors, inductors, transformers, integrated circuits, microprocessors, digital to analog converters, displays, and other types of electronic components.

Figure 6:
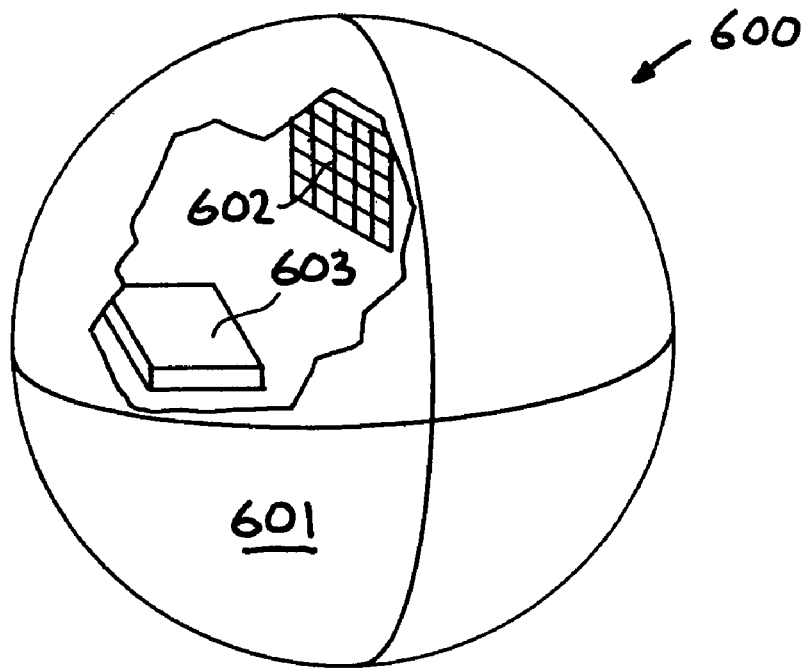
FIG. 6 illustrates another embodiment of a system constructed in accordance with the present invention.

Referring now to FIG. 6, another embodiment of a system constructed in accordance with the present invention is illustrated. The system is generally designated by the reference numeral 600. The system 600 comprises a flexible polymer body 601 in the shape of a sphere. A solar cell 602 and a MEMS sensor 603 are operatively connected inside the spherical flexible polymer body 601. The system 600 provides a distributed sensor. The system 600 can be distributed by dropping many of the systems 600 from a car or a plane and they will distribute themselves by bouncing around. The curved spherical polymer surface serves as a lens, focusing radiation from the sun onto solar cell 602. It is essentially a smart superball.

The system 600 is made of four segments. Each of the segments is a quarter sphere. The solar cell 602 and the MEMS sensor 603 are positioned inside the spherical flexible polymer body 601. The spherical flexible polymer body 601 is produced by assembling the four segments 602, 603, 604, and 605 together.

Figure 7:
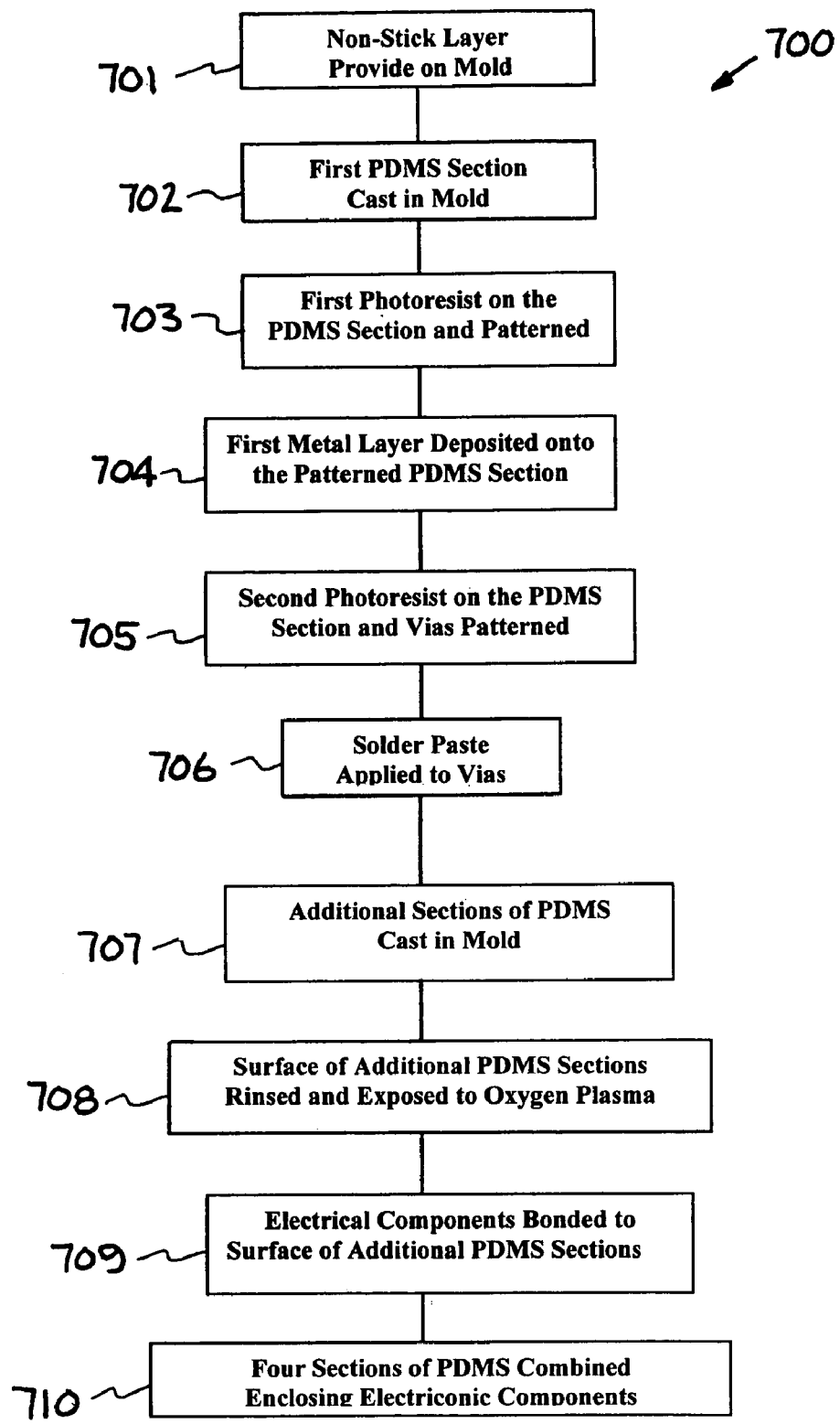
FIG. 7 illustrates a method of producing an electronic system.

Referring now to in FIG. 7, a method of producing the electronic system 600 shown in FIG. 6 is illustrated. Step 701 comprises the deposition of gold (or platinum) onto a quarter spherical mold. This allows for removal of the PDMS from the mold after processing.

In step 702, a flexible polymer layer is cast into the mold. The polymer used for the flexible polymer body has characteristics that include at least one of being fluid, resinous, rubbery, stable in high temperatures, and hydrophobic. The flexible polymer used for the polymer body 601 is a silicone. The silicone is poly(dimethylsiloxane) known as PDMS. PDMS has very low water permeability and protects the electronic components from the environment. PDMS is flexible and can be cast into various shapes. It is transparent, stretchable, resinous, rubbery, stable in high temperatures and provides numerous applications for the electronic system 600 produced by the method 700.

In step 703 the process of forming the electrical circuit lines and the antenna of the electronic system 600 is initiated. A photoresist (AZ®1618, Clariant) is spun onto the PDMS section surface at 1000 rpm for 20 seconds and baked at 60° C. for 20 minutes and then the temperature is brought down slowly (30 min to ramp temperature down) to room temperature to avoid cracking in the photoresist. Prior to photoresist application, the section is placed in an oxygen plasma to oxidize the surface. This allows the resist to wet the PDMS surface eliminating beading and ensuring the formation of a smooth and uniform coat of photoresist on the polymer surface. The substrate is placed in the oxygen plasma for 1 minute at an RF power of 100 Watts with oxygen flowing at 300 sccm. The photoresist features are then UV exposed at 279 mJ and developed in AZ developer 1:1 for 70 seconds. Then the section is rinsed under a slow stream of water gently and quickly and then dried using nitrogen. The section is placed for a second time in the oxygen plasma to activate the newly exposed PDMS surface, and promote adhesion of the metal.

In step 704 a 150 nm gold film is e-beam evaporated onto the section using 20 nn of titanium as the adhesion layer. Both titanium and gold are deposited at 0.2 nm per second. The e-beam needs to be sufficiently cooled down before removing the parts. Cool down is conducted for 10 min. under vacuum and for 20 min. with system vented, but not open. The metal adheres to the PDMS surface in the regions where the photoresist was removed and the excess metal is stripped through a lift-off process by placing the section in acetone. The section is then prepared for the next step by rinsing with ethanol and drying gently. If the PDMS surface is contaminated or aged, it is soaked in 20% solution of HCl for 8 min to refresh the surface.

In step 706 the process of forming the vias to connect the electrical circuit lines to the electronic components of the electronic system 100 is initiated. A photoresist (AZ®1618, Clariant) is spun onto the PDMS section surface. The photoresist vias features are then UV exposed at 279 mJ and developed in AZ developer 1:1 for 70 sec. PDMS is spun over the photoresist features and cured at 66 C. for 24 hours. The photoresist features are gently swabbed to remove excess PDMS before stripping the resist. This ensures the complete clearance of the via regions. To strip the resist the section is soaked in acetone for 16 min. and then soaked in isoproponol for 6 min. and then rinsed with isoproponol and dried.

In step 706 conductive material is applied to the vias. This material can be conductive silicone adhesive, conductive ink or solder paste. An automated dispenser or applicator machine is used to deposit precise amounts of material in the via locations. Alternatively, the metal can be screen-printed or squeegeed into the vias using liquids or pastes such as conductive inks, or liquid ink can be injected into channels formed in the first PDMS layer. As another option, metal such as gold can be electroplated in the PDMS vias to form an array of electrical contacts.

In step 707 additional sections of PDMS are cast in a mold. Gold (or platinum) is deposited onto the quarter spherical mold. This allows for removal of the PDMS from the mold after processing.

In step 708, the surface of the additional PDMS layer is rinsed with ethanol and exposed to an oxygen plasma. This activates the surface in preparation for bonding the electronic components to the electronic components. Bonding steps are performed in a nitrogen environment in order to extend the lifetime of the activated surface.

In step 709, one or more components are bonded to the PDMS surface in order to make electrical contact and to seal and protect the devices from the environment.

In step 710, the spherical flexible polymer body 701 is produced by assembling the four segments 602, 603, 604, and 605 together. The solar cell 602 and the MEMS sensor 603 are located inside the spherical flexible polymer body 601. The solar cell and MEMS sensors are components bonded to the surface of one of the sections. Cavities are formed in the opposing sections to accommodate these components. The system 700 provides a distributed sensor. The system 600 can be distributed by dropping many of the systems 600 from a car or a plane and they will distribute themselves by bouncing around. The round shape of the clear polymer body serve serves as a lens, focusing solar energy onto the solar cell 602 when it is distributed. It is essentially a smart superball.

Figure 8:
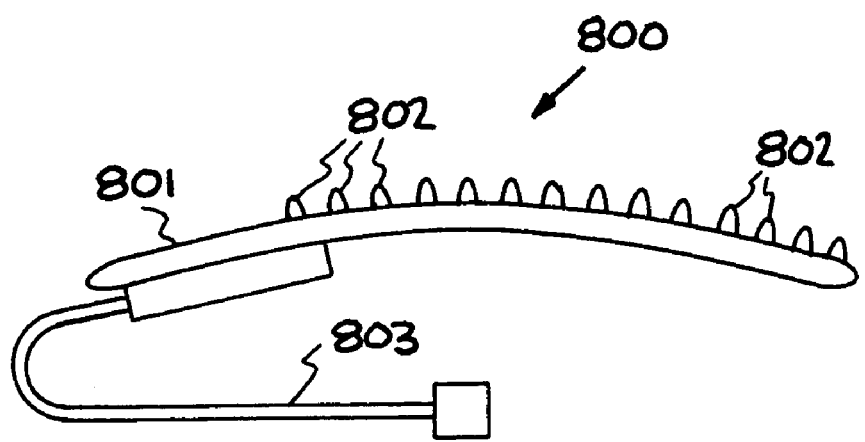
FIG. 8 illustrates another embodiment of a system constructed in accordance with the present invention.

Referring now to FIG. 8, an electrode array is illustrated. The electrode array is designated generally by the reference numeral 800. The electrode array 800 can be attached to the skin and can be implanted. The electrode array comprises electrodes 802 and conductive leads 803 operatively connected to a flexible polymer body 801. The electrode array 800 can conform to various shapes and the electrode array 800 is stretchable and biocompatible. In one embodiment, the device has at least one electronic chip bonded to it to control the electrical potential of the electrodes, or monitor the electrical behavior of cells. In another embodiment sensors such as accelerometers are bonded to the device.

The electrode array 800 has many uses. For example the electrode array 800 can be used for directly stimulating cells. The electrode array can also be used for receiving signals from cells. The electrode array 800 provides a system that is implantable and can be used for surgical insertion. The electrode array 800 can be attached to the surface of the skin or other tissue. The electrode array 800 can be used in other ways. Other applications of the electrode array 800 include use as a flex circuit. The electrode array 800 has uses including deep brain stimulation for therapy of diseases such as Parkinsons disease, muscle control, audio prosthesis, a general interface between a person and a computer, sensor, or machine, and formed biological sensors and stimulators for interfacing with the human body. These can be used for applications ranging from disease diagnosis and therapy to sensors for virtual reality simulators, to devices for enabling the human body to perform beyond normal capabilities, for example through IR vision, or receiving information directly to the brain by wireless transmission.

An implantable electrode array is shown in U.S. Pat. No. 4,573,481 by Leo A. Bullara, patented Mar. 4, 1986. The disclosure of this patent is incorporated herein in its entirety by reference. A directional programming for implantable electrode arrays is shown in U.S. Pat. No. 6,052,624 for by Carla M. Mann, patented Apr. 18, 2000. The disclosure of this patent is incorporated herein in its entirety by reference.

The electrode array 800 comprises a body 801 comprising at least in part a flexible polymer. The polymer has the ability to conform to various shapes of the tissue. In one embodiment the polymer is compliant. In another embodiment the polymer is silicone. In another embodiment the polymer is an elastomer. In another embodiment the polymer is an elastomer that is flexible and stretchable. In another embodiment, the polymer is silicone rubber. In another embodiment the elastomer is poly(dimethylsiloxane) or PDMS.

Electrodes 802 are embedded in the body 801. Conductive leads 803 are connected to the electrodes. The electrodes are useful for stimulating cells and recording signals from cells. In one embodiment the electrode array transfers an electrical signal directly to the brain. The flexible nature of the polymer allows the device to float freely with the brain inside the skull.

In addition to the electrode array 800, the present invention provides a method of fabricating a flexible electrode array. The method comprises the steps of providing a silicone layer on a substrate, providing a metal layer on said silicone layer, providing a second layer of silicone on said silicone layer, operatively connecting at least one electronic unit to said metal layer and said second silicone layer, and removing said electronic apparatus from said substrate. In one embodiment, a handle wafer is coated with metal to prevent adhesion of the silicone to the handle wafer. The first silicone layer is deposited. A second metal layer is deposited and patterned. Then the next PDMS layer is deposited and patterned to expose the conductive seed layer to form electrodes. The electrodes are either electroplated from the seed layer, or deposited in the form of conductive ink or paste. One embodiment includes the step of directly embedding an electrical connector into the device to interface with electronics. Another embodiment includes the step of spin-coating or casting a PDMS capping layer on to the first PDMS layer. Another embodiment includes the step of bonding a PDMS capping layer to the first PDMS. In one embodiment the metal electrodes are biocompatible. In another embodiment the electrodes are gold. In another embodiment the electrodes are platinum. In another embodiment, the electrodes are iridium. In another embodiment, the electrodes are iridium oxide. In another embodiment the electrodes are made of a conductive polymer material. In another embodiment, the electrodes are made of conductive ink or paste form of carbon, platinum, iridium, or iridium oxide particles bound by a polymer or epoxy matrix. In another embodiment, the electrodes are made of conductive ink or paste formed of a combination of conductive particles in a polymer or epoxy matrix. In another embodiment a pre-patterned or formed PDMS layer is cast in place with a mold. In another embodiment the electrodes are electroplated using gold. In another embodiment the electrodes are electroplated using platinum. In another embodiment the electrodes are electroplated using iridium. In another embodiment the electrodes are electroplated using iridium oxide. In another embodiment a pre-patterned or formed PDMS layer is bonded to the handle wafer. In another embodiment a step of patterning conducting lines on the PDMS is performed. The conducting lines are patterned using a combination of thin film deposition and photolithography. In another embodiment the step of patterning conducting lines on the PDMS is conducted using photolithography. In another embodiment the step of patterning conducting lines on the PDMS is conducted using shadow masking. In another embodiment, the step of patterning conducting lines on the PDMS is conducted using screen printing techniques to selectively apply conductive ink or paste. An embodiment includes doping the PDMS with metal or other conducting particles to selectively render it conductive. An embodiment includes removing the PDMS from the handle wafer.

The flexible electrode array 800 is produced by implementing various processing steps on a substrate. A conductive material is deposited on a handle wafer and various processing steps are taken to complete the flexible electrode array 800. The flexible electrode array includes a poly (dimethylsiloxane) or PDMS (a form of silicone rubber) substrate with embedded electrodes 802 and conductive leads 803. The substrate is initially positioned on a handle wafer. The electrode system can be constructed using a combination of electroplating, and screen printing, and deposition, and patterning of the thin film metals on PDMS.

Electrode Fabrication Process

1. Deposit gold (or platinum) onto a handle wafer, preferably round wafers to make later processing steps easier. The gold layer allows for removal of the PDMS from the substrate after processing.
2. Mix PDMS 10:1 ratio resin to curing agent. Mix well and degas.
3. Spin on first PDMS layer.
4. Cure PDMS 24 hrs at 66° C.
5. Allow PDMS to cool.
6. Patterning Conductive Metal Lines Using Lift-Off Process (See "Process for Patterning Conductive Metal Lines Using Lift-Off Process" below).
7. Spin on thick photoresist.
8. Expose through mask and develop to produce the patterned photoresist.
9. Mix PDMS 10:1 ratio resin to curing agent. Mix well and degas. Activate the surface of the first PDMS layer in an oxygen plasma.
10. Spin on or cast desired thickness of PDMS onto the patterned photoresist on the handle wafer.
11. Let PDMS settle at room temperature before curing. This allows PDMS to separate from the photoresist.
12. Cure PDMS 1 hr at 66° C.
13. Allow PDMS to cool.
14. Remove remaining photoresist using acetone. This results in a patterned PDMS layer on top of the handle wafer with a partially exposed metal seed layer.
15. Electroplate gold or platinum through the patterned PDMS to form electrodes and contacts for electronic chips and other components.

Process for Patterning Conductive Metal Lines Using Lift-Off Process

1. Oxidize the PDMS surface for 1 min. at 100 watts RF power.
2. Spin on AZ1518 Photoresist at 1000 rpm for 20 sec.
3. Soft bake the resist at 60° C. for 10 min then bring down temperature to 45° C. for 10 min and then bring down temperature to 30° C. for 10 min. (Lowering the temperature slowly minimizes cracking in the photoresist).
4. Expose for 15 sec. through mask.
5. Develop in AZ developer for approximately 1 min.
6. Deposit metal using electron-beam evaporator.
7. Deposit 200 angstroms of titanium as the adhesion layer at 2 angstroms/sec.
8. Deposit 1000 angstroms of gold as the conductive metal at 2 angstroms/sec. Platinum can be used as an alternative to gold.
9. Deposit 200 angstroms of titanium on top of the gold to provide an adhesion layer for the 2nd PDMS layer that will be deposited later.
10. Following metal deposition place in acetone to remove excess metal through a lift-off process, but do not shake or stir as this may cause the PDMS to lift off of the substrate. Apply PDMS around the edges of the wafer to ensure that the PDMS membrane remains attached to the substrate.
11. Gently rinse with acetone and isopropyl alcohol and set on a flat surface. Air dry.

Figure 9:
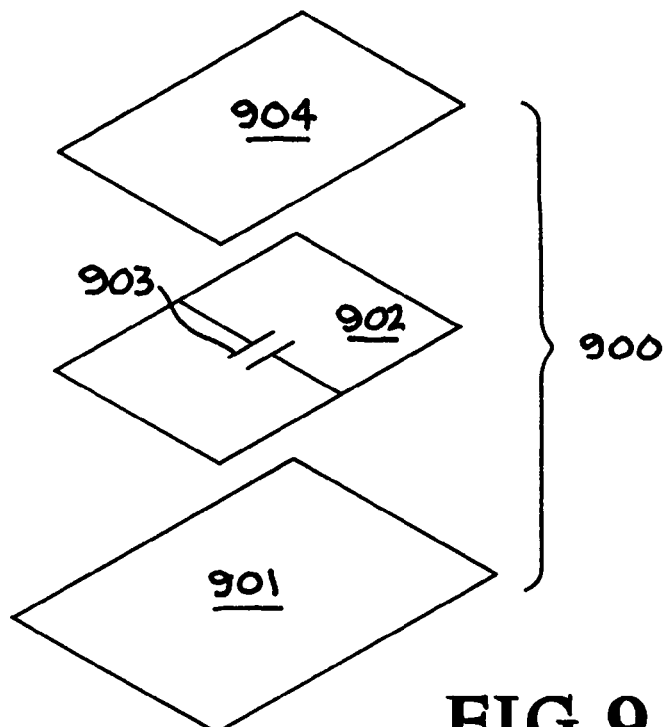
FIG. 9 illustrates another embodiment of a system constructed in accordance with the present invention.

Referring now to in FIG. 9, another embodiment of a system constructed in accordance with the present invention is illustrated. The system is generally designated by the reference numeral 900. The system 900 comprises a flexible polymer body 902 & 904 and a capacitor 903 operatively connected to the flexible polymer body. The system 900 provides an integrated electronic system that can be described as a "peel and stick" electronic component system. The system 900 can be visualized as a thin, clear, and flexible unit similar to the clear "peel and stick" tags garages place on an automobile's windshield after the car has been serviced to remind the owner of the automobile when the next servicing is due. The thin, clear, and flexible "peel and stick" electronic apparatus 900 can be very small and inconspicuous.

The system 900 comprises a flexible polymer body 902 & 904. The flexible polymer body can be a number of polymers whose properties are determined by the organic groups and that have characteristics that include one or more of being fluid, resinous, rubbery, stable in high temperatures, and hydrophobic. The flexible polymer body unit comprises a polymer substrate 902 that serves as a polymer-based platform for integrating and packaging the electronic components 903. The electronic components 903 are integrated into the flexible polymer body. The underside of the substrate unit 902 is a peel and stick surface that can easily be affixed to other surfaces. In manufacturing, after curing the PDMS body surface is tacky and will stick to any clean, smooth surface such as electrical equipment, circuit boards, and a wide variety of other surfaces. An adhesive may be included on the underside surface or the underside surface may be attached to other surfaces by other means. The small, thin, clear, flexible, peel and stick, electronic apparatus 900 is very inconspicuous and durable. The flexible polymer body protects the electronic components 903 from the environment. The system 900 can provide a wide variety of other electronic components instead of the capacitor 903. For example, electronic components that can be used in place of capacitor 903 include resistors, inductors, transformers, integrated circuits, microprocessors, digital to analog converters, displays, and other types of electronic components.

Figure 10:
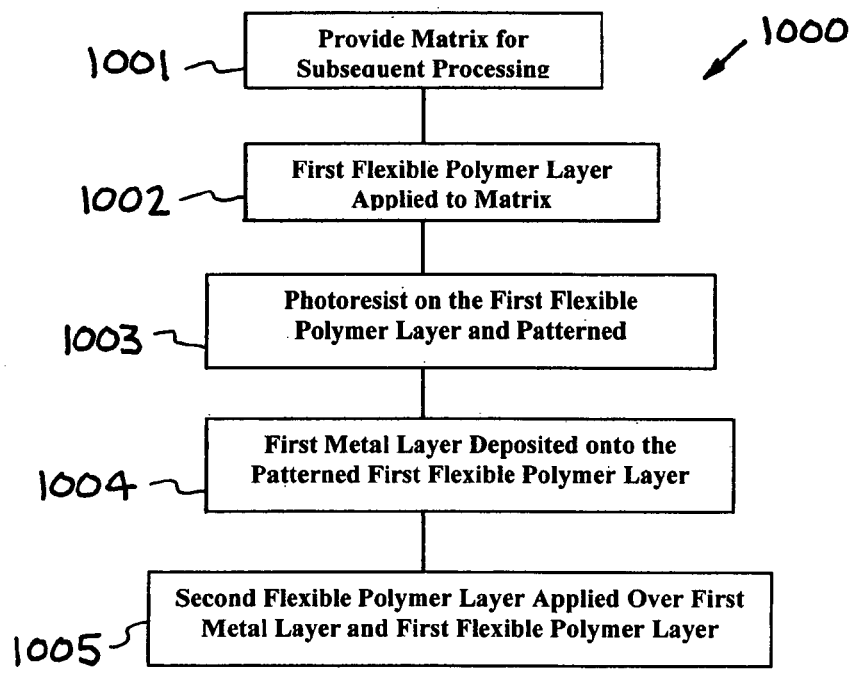
FIG. 10 illustrates a method of producing an electronic system.

Referring now to in FIG. 10, a method of producing the electronic system 900 shown in FIG. 9 is illustrated. In step 1001 (Provide Substrate for Subsequent Processing), a substrate for subsequent processing is provided. The substrate may be a handle wafer, a mold, or other form for subsequent processing steps. A silicon handle wafer is a convenient substrate because it is flat, stable, routinely used in microfabrication applications, and is readily available. Other materials such as glass, plastic, or ceramic could be used as well.

In step 1002 (First Flexible Polymer Layer Applied to Substrate), a first flexible polymer layer is applied to the substrate. Before the first flexible polymer layer is applied, a titanium/gold layer can be deposited onto the substrate if it is glass or silicone to prevent adhesion of the polymer. The polymer used for the first flexible polymer layer and the second flexible polymer layer has characteristics that include at least one of being fluid, resinous, rubbery, stable in high temperatures, and hydrophobic. The flexible polymer used as polymer layers of the electronic apparatus 900 is a silicone. The silicone is poly(dimethylsiloxane) known as PDMS is one form of silicone. PDMS has very low water permeability and protects the electronic components from the environment. PDMS is flexible and will conform to curved surfaces. It is transparent, stretchable, resinous, rubbery, stable in high temperatures and provides numerous applications for the electronic system 900 produced by the method 1000.

In step 1003 (Photoresist on the First Flexible Polymer Layer and Patterned), the process of forming the electrical circuit lines that form the capacitor of the electronic system 900 is initiated.

A photoresist (AZ®1518, Clariant) is spun onto the PDMS membrane surface at 1000 rpm for 20 seconds and baked at 60° C. for 20 minutes. The temperature is brought down slowly (30 min to ramp temperature down) to room temperature to avoid cracking in the photoresist. Prior to photoresist application, the wafer is placed in an oxygen plasma to activate the surface. This allows the resist to wet the PDMS surface preventing beading and ensuring the formation of a smooth and uniform coat of photoresist on the polymer surface. The substrate is placed in the oxygen plasma for 1 minute at an RF power of 100 Watts with oxygen flowing at 300 sccm. The photoresist features are then UV exposed at 279 mJ and developed in AZ developer mixed 1:1 with water for 70 sec. Then the wafer is rinsed under a gentle stream of water and dried using N2. The wafer is placed for a second time in the oxygen plasma to activate the newly exposed PDMS surface, and promote adhesion of the metal, which is deposited in the next step.

In step 1004 (First Metal Layer Deposited onto the Patterned First Flexible Polymer Layer) A 150 nm gold film is e-beam evaporated onto the wafer using 20 nm of titanium as the adhesion layer. Both titanium and gold are deposited at 0.2 nm per second. The e-beam needs to be sufficiently cooled down before removing the parts. Cool down is conducted for 10 min. under vacuum and for 20 min. with the system vented, but not open. The metal adheres to the PDMS surface in regions where the photoresist was removed, and the excess metal is removed through a lift-off process by placing the wafer in acetone. The wafer is then prepared for the next step by rinsing with ethanol and drying gently. If the PDMS surface is contaminated or aged, it can be refreshed by soaking in a 20% solution of HCl for 8 min.

In step 1005 (Second Flexible Polymer Layer Applied Over First Metal Layer and First Flexible Polymer Layer), a second layer of PDMS is applied over the first flexible polymer layer and the electrical circuit lines that connect to the capacitor. PDMS is flexible, transparent, stretchable, resinous, rubbery, stable in high temperatures, and provides numerous applications for the electronic system 900 produced by the method 1000. The final step is to bond on the capacitor and other electrical components.

Figure 11:
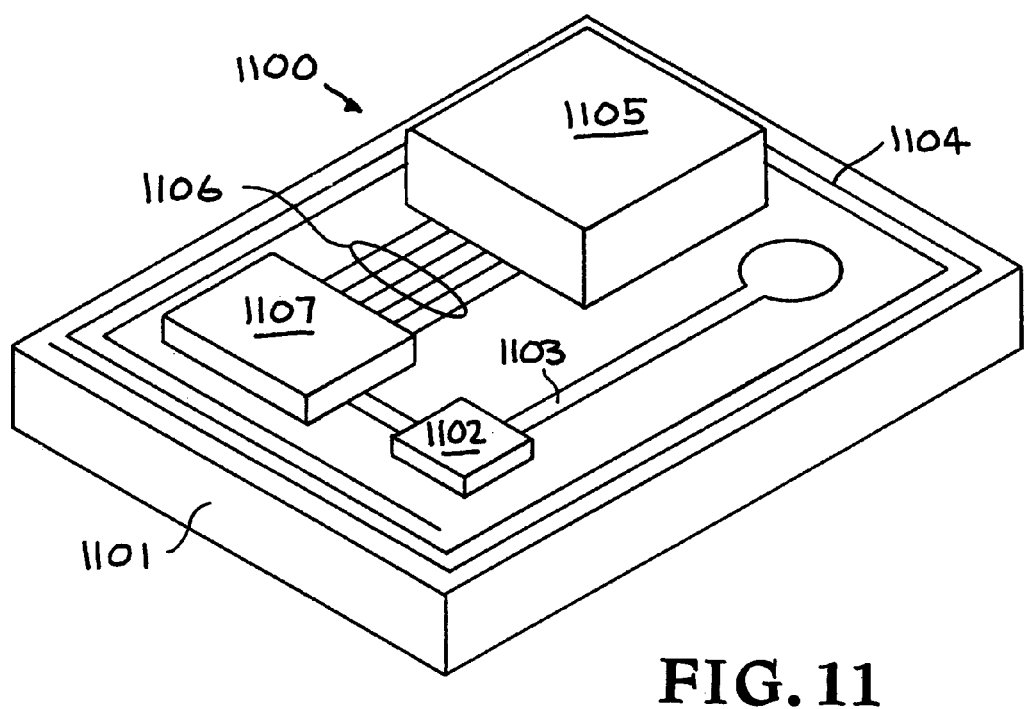
FIG. 11 illustrates another embodiment of a system constructed in accordance with the present invention.

Referring now to in FIG. 11, another embodiment of a system constructed in accordance with the present invention is illustrated. The system is generally designated by the reference numeral 1100. Integrated microsystems will play an increasingly important role in Homeland Security applications. Examples include microfluidic systems for chemical and biological threat detection, distributed sensors for tracking terrorist activities, radiation detectors, and cargo container monitoring devices. These applications require small, low cost, rugged, field-operable devices. Deployable sensors with wireless communication capability are required for numerous counter-terrorism and intelligence applications. Examples include monitoring cargo shipments, tracking troop, individual personnel, and vehicle movement, and detecting chemical and biological signatures associated with various threats. These sensor modules must meet several requirements for widespread deployment. They need to be inexpensive, rugged for air-drop deployment and abusive conditions, inconspicuous, able to withstand severe environmental factors (temperature extremes, water submersion), and self-sufficient (integrated power, electronics, sensing, and communications).

The system 1100 comprises a PDMS body 1101, an optical sensor 1102 operatively connected to the PDMS body 1101, a microfluidic channel 1103 operatively connected to the PDMS body 1101, a MEMS sensor 1105 operatively connected to the PDMS body 1101, and an Application-Specific Integrated Circuit (ASIC) 1107 operatively connected to the PDMS body 1101. Metal traces 1106 are integrated into the PDMS body 1101 that connect the optical sensor 1102, the Application-Specific Integrated Circuit 1107, and the MEMS sensor 1105. An antenna 1104 facilitates communication with a remote receiver.

The underside of the substrate unit 1101 is a peel and stick surface that can easily be affixed to other surfaces. In manufacturing, after curing the PDMS body surface is tacky and will stick to any clean, smooth surface such as electrical equipment, circuit boards, and a wide variety of other surfaces. An adhesive may be included on the underside surface or the underside surface may be attached to other surfaces by other means. The small, thin, clear, flexible, peel and stick, electronic apparatus 1100 is very adaptable and durable. The flexible polymer body protects the components from the environment.

The system 1100 provides an integrated electronic system that can be described as a "peel and stick" electronic component system. The system 1100 can be visualized as a thin, clear, and flexible unit similar to the clear "peel and stick" tags garages place on an automobile's windshield after the car has been serviced to remind the owner of the automobile when the next servicing is due. The thin, clear, and flexible "peel and stick" electronic apparatus 110 can be very small and adaptable.

The system 1100 comprises a polymer-based platform that will enable the development of hybrid microsystems with integrated sensors, electronics, optical elements, power, and microfluidics. The platform is capable of incorporating off-the-shelf components as well as custom fabricated devices, and features a low cost packaging approach. Polydimethylsiloxane (PDMS) serves as the integration backbone, with microfluidic structures molded into the silicone polymer, and other components such as silicon sensors and circuits directly bonded to the PDMS, forming a leak-proof seal. Electrical traces are patterned on the PDMS to interconnect the various components. The ACIC chip 1107 and the other components are irreversibly bonded to the PDMS substrate 1101 to make electrical contact to the metal traces 1106 and seal the device 1100, protecting active elements from the environment.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of fabricating an electronic apparatus, consisting essentially of the steps of:
    providing a silicone layer on a matrix,
    providing a metal layer on said silicone layer,
    providing a second layer of silicone on said silicone layer and said metal layer,
    providing at least one electronic unit connected to said metal layer,
    providing a third layer of silicone on said second layer of silicone and said electronic component, and
    removing said electronic apparatus from said matrix.

2. The method of fabricating an electronic apparatus of claim 1 wherein said silicone layer, said second layer of a silicone, and said third layer of silicone comprise poly(dimethylsiloxane).

3. The method of fabricating an electronic apparatus of claim 1 wherein said silicone layer, said second layer of silicone, and said third layer of silicone provide a thin flat polymer body.

4. The method of fabricating an electronic apparatus of claim 1 wherein said at least one electronic unit comprises an electrode array.

* * * * *